United States Patent [19]

Singh et al.

[11] Patent Number: 4,782,817
[45] Date of Patent: Nov. 8, 1988

[54] VENTRICULAR SUPPORT SYSTEM

[75] Inventors: Param I. Singh, Lexington; William J. Bolt, Beverly; Dana C. Sawyer, Wakefield, all of Mass.

[73] Assignee: Abiomed Cardiovascular, Inc., Danvers, Mass.

[21] Appl. No.: 55,648

[22] Filed: May 29, 1987

[51] Int. Cl.$^4$ .......................... A61M 1/03; A61F 1/24
[52] U.S. Cl. ........................................ 600/17; 417/22; 417/394; 604/67
[58] Field of Search ...................... 128/1 D; 604/4, 67; 417/300, 389, 394, 19, 20, 22

[56] References Cited

U.S. PATENT DOCUMENTS

| | | | |
|---|---|---|---|
| 3,376,660 | 4/1968 | McGinnis | 35/17 |
| 3,639,084 | 2/1972 | Goldhaber | 128/1 D |
| 3,718,044 | 2/1973 | Joyce, Jr. et al. | 73/223 |
| 3,955,557 | 5/1976 | Takagi | 128/1 D |
| 4,080,958 | 3/1978 | Bregman et al. | 128/1 D |
| 4,212,589 | 7/1980 | Bosio | 417/394 |
| 4,353,220 | 10/1982 | Curwen et al. | 417/22 |
| 4,465,063 | 8/1984 | Nielsen et al. | 128/1 D |
| 4,583,525 | 4/1986 | Suzuki et al. | 128/1 D |
| 4,611,578 | 9/1986 | Heimes | 128/1 D |
| 4,662,355 | 5/1987 | Pieronne et al. | 128/1 D |

FOREIGN PATENT DOCUMENTS

| | | | |
|---|---|---|---|
| 2501552 | 7/1975 | Fed. Rep. of Germany | 604/4 |
| 2658104 | 1/1977 | Fed. Rep. of Germany | |
| 733688 | 5/1980 | U.S.S.R. | |
| 0844815 | 7/1981 | U.S.S.R. | 604/4 |
| 2004942A | 4/1979 | United Kingdom | |

Primary Examiner—Dalton L. Truluck
Attorney, Agent, or Firm—Lahive & Cockfield

[57] ABSTRACT

An extracorporate ventricular support system includes a two bladder pump employing continuous gravity fill to the first bladder, while the second bladder is pneumatically driven to produce a pulsatile blood flow. A processor responds to air flow in the pneumatic drive line to control the pump through an electromagnetic valve supplying pressurized air. The program controls the output of blood volume per stroke to meet a target value.

8 Claims, 4 Drawing Sheets

VENTRICULAR SUPPORT SYSTEM

BACKGROUND OF THE INVENTION

This invention relates in general to cardiac assist systems and more particularly to an extracorporeal system employing a gravity filled disposable blood pump automatically controlled to continuously optimize blood flow asynchronously. Cardiac assist systems are employed in a number of clinical situations including post cardiotomy ventricular dysfunction, post myocardial infarct, cardiogenic shock, as well as a bridge to heart transplant. Many of these systems are, at best, semi-automatic in that they require adjustment of pump controlled variables such as beat rate, systolic duration, drive pressure, vacuum pressure, flow rate, and timing in order to assure proper blood flow in response to changing conditions in the patient.

One such system is described in German Application No. 2658104 filed Dec. 22, 1976 and published Jan. 12, 1977. That reference describes a system employing a diaphragm pump with a diaphragm position transducer providing a signal indicating when the diaphragm is fully collapsed or fully extended. This transducer signal is used to operate an electromagnetic valve which either allows the pneumatic flow to move toward the diaphragm, tending to collapse the wall and thus provide a systolic pumping action or to decrease pressure allowing blood to fill the pump. The system system is arranged so that the pump always pumps at the lowest possible frequency. Thus a higher filling rate at the input causes the pump to beat faster.

A second prior art method is described in USSR inventor's Certificate No. 733688 filed Nov. 23, 1977 and published May 15, 1980 entitled "Device For Indirect Control Of Performance Of Artificial Heart With External Pneumatic Drive". This certificate describes a system for generating a signal controlling the rate of change of gas pressure and generating a signal correcting for the compressibility factor of the gas in a pneumatically driven heart pump. An algebraic summer sums the signal indicative of volume flow rate together with a signal indicative of the derivative value of gas pressure, thereby producing a corrected signal of flow rate. To determine the stroke volume of the artificial heart, a filtered signal from the summer is transferred to an integrator, the integration period of which is controlled by a specific control unit.

Other systems are described, for example, in the book "Assisted Circulation" edited by Felix Unger, Innsbruck, published by Springer-Verlag in 1979. At page 322 of that volume there is described a method of measuring pressure and flow in which a signal indicating the change of direction of the air flow and one indicating the arrival of the air flow at a zero value are generated. The two signals are combined and analyzed to produce values for the stroke volume in air, the heart frequency, the systolic duration, the difference of systolic and diastolic pressures, the center of the area of systolic flow versus time and the center of the area of diastolic flow versus time. The real stroke volume of the pump can then be calculated with a minicomputer whose value is fed back to the surgeon.

One of the disadvantages of the prior art systems is the possibility of hemolysis of the blood cells due to an axisymmetric bladder collapsing too far during the systolic beat and thus physically compressing the blood between its walls. Additionally problems are introduced whenever the pump uses vacuum, as do many of the prior art pumps, since this can lead to collapse of the natural atrium or suction of air.

SUMMARY OF THE INVENTION

The primary object of the present invention is to provide a fully automatic control system for utilizing a gravity filled extracorporeal diaphgram pump to perform the function of the ventricles asynchronously with respect to the natural rhythm of the patient's heart, and operating at an optimum blood flow.

Broadly speaking, a pulsatile ventricular assist system is provided which can serve as a cardiac assist for either a single ventricle or both ventricles. The pump itself is located outside of the patient's body and is a disposable diaphragm type pump including a pair of chambers. The first chamber is an artificial atrium in which the bladder is passive, that is, it is not pneumatically driven, and is allowed to fill on a continuous basis from the patient under the influence of gravity alone. The second chamber, which is connected by a trileaflet valve to the first, also includes a collapsible bladder, but in this instance the bladder is pneumatically driven and performs a pumping action to create artificial systole. In the second chamber, during systole, a gas flow is provided through an electromagnetic valve to collapse the bladder ejecting blood through a second trileaflet valve to the patient, while in artificial diastole the valve provides for venting of the air space surrounding this bladder to atmosphere, thereby allowing the gravity flow of blood from the upper chamber into it.

The key to the invention is the pumping control system which provides completely automatic control of the pump, based upon the measurement of air flow in the pneumatic line from the gas supply through an electromagnetic valve to the second chamber of the diaphragm pump. The volumetric flow rate signal generated in the pneumatic line is used to terminate the diastolic operation by detecting when the flow rate drops below a specific value indicative of substantial emptying of the first bladder's contents into the second active chamber. The end of this diastolic period, in normal circumstances, not only terminates the diastole but also initiates the systole through the action of the electromagnetic valve. The systolic period is run for an adjustable time duration, which is recalculated for every beat and provides for a maximum stroke volume of approximately eighty percent of the volume of the bladder, thereby assuring that there is no complete collapse of the bladder walls upon one another with a resultant hemolysis of the blood.

While a single pump may be employed, a pair of pumps can be employed to provide for pumping both the right and left ventricles independently.

DESCRIPTION OF PREFERRED EMBODIMENT

Figure 1:
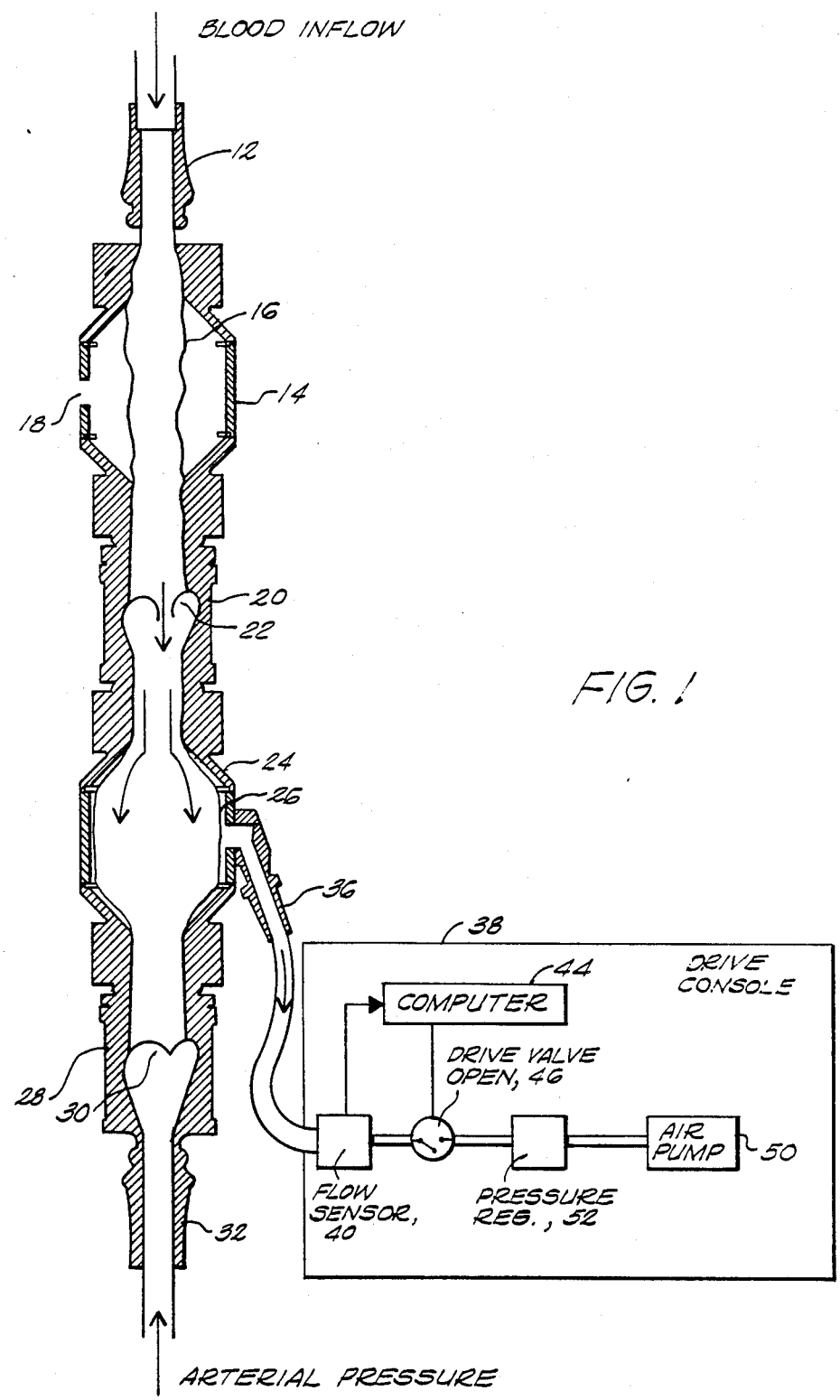
FIG. 1 is an illustration in generally diagrammatic form of a pulsatile ventricular assist system constructed in accordance for the principles of this invention shown in the configuration for pump diastole.

With reference now to FIG. 1 there is illustrated a preferred embodiment of the ventricular system of this invention configured for pump diastole, that is that portion of the cycle when the blood inflow is filling the bladder of the active portion of the pump prior to the systolic ejection of blood from the pump. The device consists of two major subsystems: a drive console 38 and a single-use disposable blood pump. The blood pump, like the natural heart, is comprised of two chambers 14 and 24 each including a flexible bladder, 16 and 26 respectively, and two valves 22 and 30. All are made from polyurethane. The upper chamber 14 acts as a filling chamber or atrium, while the lower chamber 24 acts as a pumping chamber or ventricle.

The pumping bladder 26 is isolated from the bladder 16 of the inflow chamber 14 and systemic pressures by one polyurethane trileaflet valve 22 at its entrance and a second trileaflet valve 30 at its exit. The inflow chamber 14 is connected via tubing and cannula to the natural atrium of the patient's heart. Filling of the pump is continuous and passive as a reuslt of atrial pressure and gravity. This is accomplished by lowering the device below the patient's atrial level, typically by less than 20 cm. The outflow chamber 24 is emptied by air pulses delivered from the drive console 38, and is filled from the inflow chamber blood volume as the air is vented through the console. As shown in FIG. 1, the input port 12 conveys blood from the patient into the inflow bladder 16 situated within a generally rigid walled first chamber 14. This chamber is vented through opening 18 to the atmosphere allowing, in this portion of the cycle, air to flow into the chamber while the bladder 16 is in a generally collapsed condition. It should be noted that the bladder 16 is not completely collapsed but remains open to allow blood from the blood inflow port 12 to pass through it and through the open trileaflet valve 22 contained in trileaflet valve housing 20. The blood inflow is chiefly provided by gravity. In this diastole mode, the outlet valve 30 remains closed since its bias is such that the force of the gravity and the atrial pressure is insufficient to open it. The outlet valve 30 is fluidically coupled to an output port 32 which in turn is connected to the arterial system of the patient.

The drive console 38 includes an air pump 50 which generates pressurized air coupled through a pressure regulator 52 to an electromagnetically controlled drive valve 46. The air pump will typically produce about 20-60 psi pressure, and the pressure regulator 52 is arranged to produce a pressure of approximately 250 mm Hg when operated as a left ventricle and about 200 mm Hg when operated as a right ventricle. The output of the controlled valve 46 is connected through flow sensor 40 to the pneumatic tube 36. In the position shown for diastole, however, the valve 46 does not couple the air pressure to the pneumatic tube 36, but rather blocks off the pressure from the air pump 50 and opens the pneumatic tube 36 to the atmosphere, thereby venting through tube 36 the exterior portion of chamber 24. Flow sensor 40 may be any suitable volumetric flow sensor, for example, a constricted orifice with a differential pressure measuring device. The output from the flow sensor 40 is connected to a computer 44 which contains software for controlling the operation of the entire support system. This computer provides a control signal back to electromagnetic valve 46 controlling when that valve is in the open position (as shown) or in the closed position as illustrated in FIG. 2.

During the diastolic portion of the cycle the air is driven from the exterior portion of the chamber 24 as blood fills the bladder 26 and this flow of air provides a signal from the sensor 40 to the computer 44 indicative of the flow of blood through the blood inflow into the bladder 26.

Figure 2:
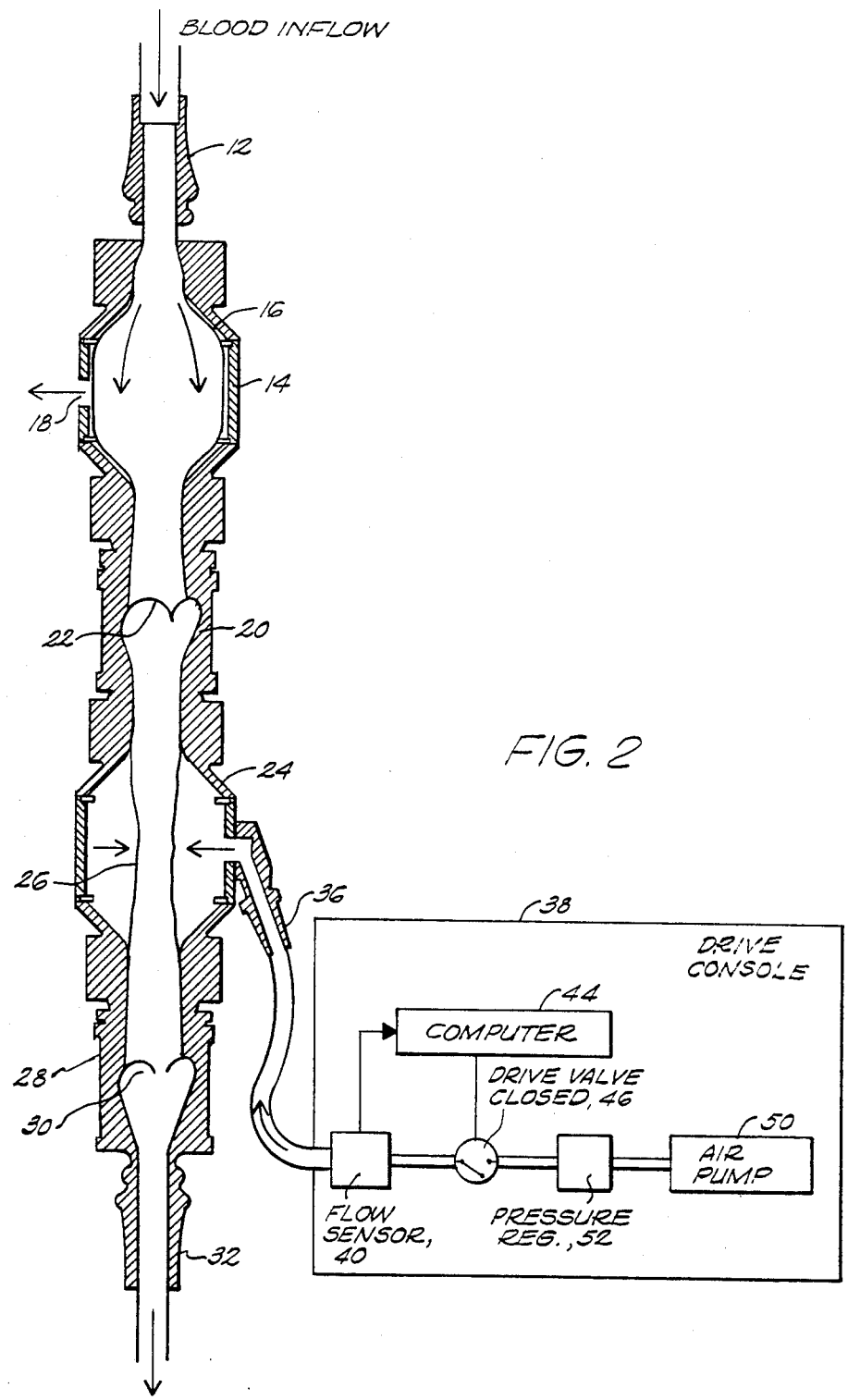
FIG. 2 is an illustration in diagrammatic form of the ventricular assist system of FIG. 1 as shown in the configuration for pump systole.

In FIG. 2 the same elements are shown in the configuration for pump systole. In this instance the valve 46 is closed, coupling pressurized air from the pump 50 through the regulator 52 and the tubing 36 to the outer portion of the chamber 24 compressing the outflow bladder 26 thereby forcing the blood which accumulated during the diastolic portion of the cycle out through the valve 30 to the arterial system of the patient. As a result of the pressurization of the internal volume of the bladder 26 the valve 22 closes so that blood can be ejected only through the outflow to the patient and not return into the first chamber bladder 16. However, even while this pressurization is proceeding, blood inflow may still be passing into the inflow bladder 16 and accumulating there in preparation for the next cycle.

All of the blood contacting surfaces of the mechanical pump, that is the input and output ports, as well as the interior surfaces of the valves and bladders are formed of a polyurethane marketed under the name Angioflex by ABIOMED, Inc. of Danvers, Mass. While this is a preferred material, any material which provides a sufficiently anti-thrombolytic surface is suitable. In a preferred embodiment the volumes of bladders 16 and 26 are each 100 cubic centimeters producing an output stroke volume of approximately 80 cubic centimeters. Typical values for the patient connections are ½ inch I.D. tubing.

Figure 3:
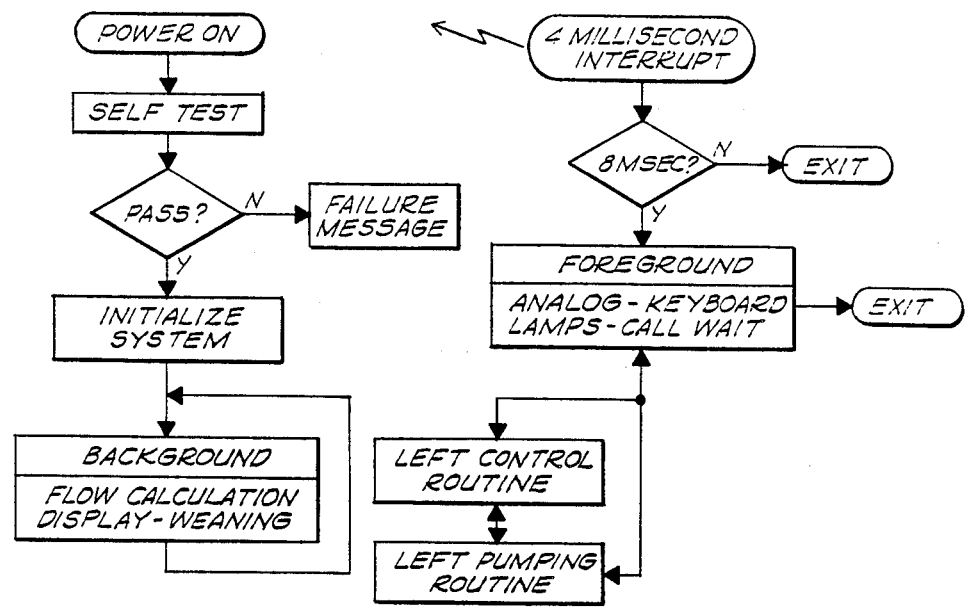
FIG. 3 is a diagrammatic illustration of software structure suitable for use in the operation of the system of FIGS. 1 and 2.

As mentioned previously the key to the operation of this assist system is the software operated computer 44. The system software operates as basically two loops, one a "background" loop the other a "foreground" loop. The basic structure of this software is illustrated in FIG. 3.

The background loop handles calculation of flow, calculation of systolic duration, alarm detection and display updating. Each cycle through the loop performs calculations, then checks alarm and keyboard monitor status. Flow is optimized by systolic interval adjustments made as a result of background calculations comparing actual to target stroke volume. The main foreground loop is initiated by a free-running 4 ms interrupt, but is only performed on alternate interrupts for an 8 ms cycle interval. During each interrupt routine, analog values are sampled and the front panel keyboard is checked for key presses. The program then switches to the control and pumping routines, testing the flow and pressure values and operating the pneumatic valves as required.

Automatic zeroing is performed by each pumping routine every 131 seconds, slightly extending diastole and performing software recalibration of the flow transducers.

Opening and closing of the pneumatic valves by the main foreground loop is performed as follows. A counter is set to the desired systolic duration, and the pneumatic valve is opened. Each 8 ms thereafter, a counter is decremented by 8 ms and tested until it becomes zero or negative, and the pneumatic valve is closed. Diastole begins by monitoring the flow value for the major drop off to occur, then waiting a blanking period, then sampling the flow value. When repeated testing shows this flow has dropped to a small specified value, diastole is considered finished, the valve is opened, and the cycle repeats.

More particularly the software controls the duration of the diastolic mode by terminating this mode when the flow rate which is measured at sensor 40 decreases below a specific level indicative of substantial filling of the bladder 26. When this occurs the computer provides a signal to the electromagnetic valve 46 changing its position from the open position in which it is venting the air from tube 36 to atmosphere to a closed position in which it receives pressurized air from the pump 50 through the pressure regulator 52. This closing of the valve initiates the systolic portion of the cycle. The software controls the duration of systole by establishing the duration as an initial predetermined time period, for example, 800 milliseconds, which is intended to be sufficient to empty eighty percent of the bladder 26, but to stop well short of complete collapse of the bladder walls which could damage the blood cells.

Generally speaking the nominal initial predetermined value selected is set to be larger than the target stroke volume so that each total beat or stroke of the pump systole time may be decremented down by a suitable value, for example, 25 milliseconds until the duration of the systolic pulse is sufficient to expel a volume of blood substantially equal to the target stroke volume. The determination of the amount of blood being ejected is made by integrating the signal from the flow sensor 40 for the previous diastolic portion of the cycle and taking the average value for the previous four beats for each beat. This average value is compared in computer 44 to the target value for stroke volume. The result of this comparison is used to determine whether the systole time should continue to be decremented. When the comparison in the computer 44 shows that the decremented period has reached a value where the actual output blood flow volume per beat equals the target value, the time duration for the systolic interval is no longer decremented.

At approximate intervals of every two minutes the time duration is incremented by a specific amount and the stroke volume compared to the target value. If the comparison shows the previous duration was correct, the duration is immediately reduced back to that value. If the new value is below target value, then the duration is again incremented two minutes later. Thus, the time duration of the systolic pulse is not incremented on every beat, but rather, by periodically being interrupted and incremented, a system is established which does not oscillate about a particular value.

Transients in pressure and flow are created and reflected in the sensed flow signals at the time of change of the electromagnetic valve position from opened to closed and closed to open. The computer is therefore programmed to ignore these transients and operate only on the values which take place thereafter.

Addressing the software system in more detail, it should be understood that the pumping cycle always begins with systole. Controlled valve 46 commences the pumping action and, as discussed above, systole ends after an adjustable time duration which is optimized in the background loop of the software to produce about the eighty to ninety percent collapse of the pumping bladder 26. This portion of the cycle also includes specific software to detect and prevent total collapse of the pumping bladder.

Still in the foreground loop, at the conclusion of the adjustable predetermined period for systole, the electromagnetic valve 46 changes to the opposite position which allows air in the exterior volume of the chamber 24 to escape through the flow sensor to the atmosphere and, as discussed above, the diastole ends when this air flow has decreased to a very small value or, alternatively when a maximum time has elapsed.

Figure 4:
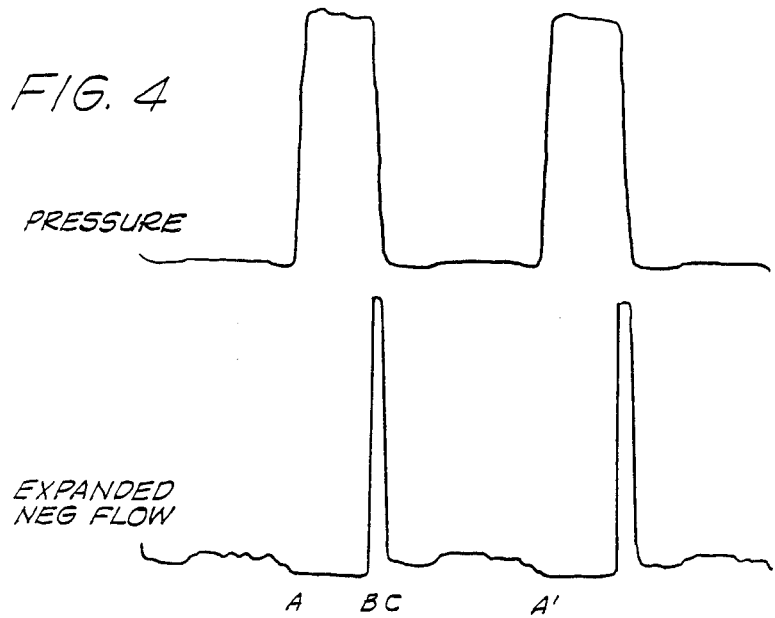
FIG. 4 is a graphical illustration of pressure and flow waveforms in the system of FIGS. 1 and 2.

In FIG. 4 typical time waveforms are shown for the pressure and expanded negative flow signals. Negative flow is defined as flow in the direction away from the chamber 24, while positive flow is defined as flow in the direction toward the chamber 24. In the diagram, point A is the time at which the electromagnetic valve 46 opens, allowing the gas to pass through the tubing 36 to the chamber 24. Thus the gas pressure increases at this point and remains elevated until termination of the systolic period when the valve 46 closes at time B. The negative flow then commences approximately at point B giving rise to a transient in the sensed negative flow which appears between times B and C. The diastolic period then follows until the decrease of the negative flow below a preset value which occurs at A', terminating the diastolic period.

In addition to the foreground loops the program includes a background loop which provides for computation and display of flow and also for the control over the adjustment of the systolic duration. As mentioned above, if the measured stroke volume differs from the target value, the duration of the systolic period is adjusted accordingly. Provision is made in the program to prevent the systolic beat duration from decreasing below a minimum safe value. Using the described arrangement the systolic duration would require approximately one-half hour to move from minimum to maximum. On the other hand, the systolic duration can decrease from maximum to minimum in less than two minutes. In the practical situation neither situation is likely to obtain.

In order to determine flow, data is obtained during the diastolic portion of the beat. The differential pressure transducer 40 generates a signal whose polarity and amplitude represent the flow through the sensor. The values of the sensor are sampled every eight milliseconds. Since the differential pressure signal from the sensor 40 is assumed to be proportional to the square of the air flow velocity, the integral of this value (which determines the volumetric flow velocity per beat) is computed as a value which is proportional to the square root of each data point.

The actual flow integral measured in foreground is adjusted to remove the exponential artifact due to the transient at depressurization which is done by computing the area under an exponential curve fitted to the initial portion of the artifact. The adjusted value of the integral is accumulated for four beats. After the fourth beat, the accumulated sum of the integrals is converted to a flow reading which is used to compute the running average flow value. This average is calculated by adding each new four beat sum to the previously calculated value then dividing the total by two. It is this average of flow value which is used as the basis for systolic period duration as well as for alarms to indicate that the flow has fallen below a predetermined lower minimum level. There is also a low pressure alarm if the systolic line pressure, based on the four beat average, does not reach predetermined acceptable levels. In addition to the low pressure alarms, there is a high pressure alarm if the four beat average systolic line pressure exceeds a specific value.

The pumping program described above is for normal operation. The system can also be manually converted to a weaning mode in which the total flow volume produced over a period of time by the pump is set to any selected one of a group of values less than would result by allowing the pump to operate in the normal mode. This weaning mode is used to gradually shift the pumping load of the blood onto the patient's own heart. This is achieved by varying the beat rate by arbitrarily extending the length of diastole until the total length of the beat is a value sufficient to have the average flow output volume from the support system equal to the selected amount for the weaning procedure. If, during the weaning mode, the blood volume is below this value, the system automatically increases the beat rate until the duration of each beat is sufficient to produce the target value of the stroke volume, exactly as it occurs in the non-weaning mode.

Figure 5:
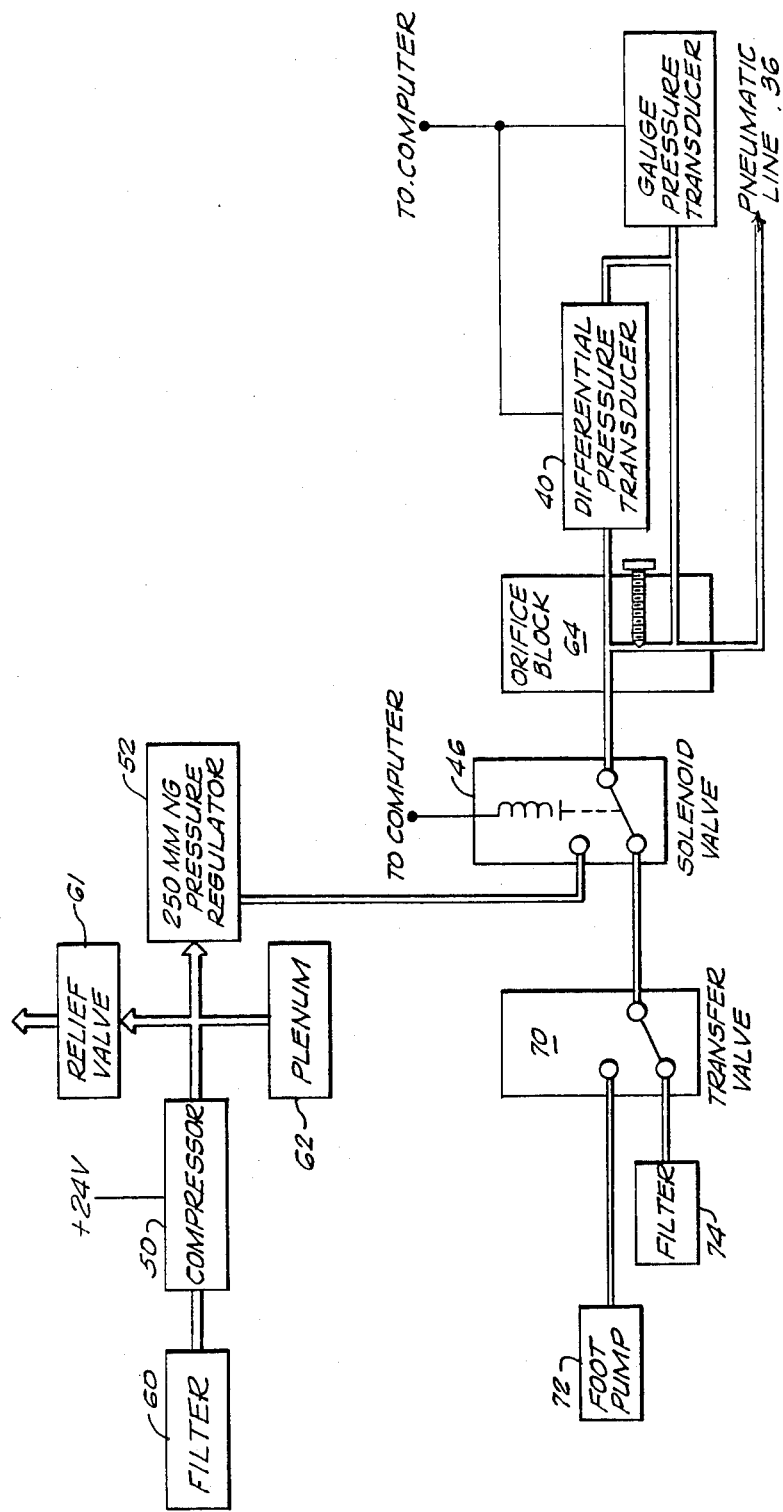
FIG. 5 is an illustration generally in block diagrammatic form of an electromechanical subsystem for the ventricular assist system in accordance with FIGS. 1 and 2.

FIG. 5 is an illustration of the electromechanical elements of the cardiac system of this invention. The air compressor 50, which has a filter 60 at its intake to filter the input air, provides output pressure to regulator 52. A relief valve 61 is a safety relief in the event that the pressure from the compressor exceeds 65 psi. Plenum 62 provides a reservoir for ensuring that a relatively high flow rate of the output gas from the pressure regulator 52 is supplied to the input of the two position solenoid valve 46 which is controlled from computer 44. The solenoid valve is open in closed position and therefore does not pass the pressurized air from regulator 52 to the pump connector 36. Thus, in the illustration as shown, the system is in the second position of the solenoid valve in which air from the pump connector 36 passes through the orifice block 64 to transfer valve 70 and thence through filter 74 to the outside atmosphere. The flow of air in this negative direction is measured by virtue of the differential pressure transducer 40 measuring the pressure drop across the orifice block, which is indicative of the flow velocity. The gauge pressure transducer 66 provides an output indicating to the computer 44 changes in pressure in chamber 24. When the solenoid valve 46 is actuated, closing the valve, then the high pressure gas from regulator 52 is coupled directly to the pump connector 36.

In addition to the elements described, the transfer valve 70 is included to provide for emergency operation of the entire cardiac system by means of a foot pump 72. Thus, if the compressor 50 should fail, the transfer valve 70 is actuated to connect the gas line 36 directly to foot pump 72, which can be manually operated in an emergency to continue supplying the pressure necessary to operate the cardiac assist system.

While the system has been described generally as a single pump arrangement, it will be understood that a pair of pumps entirely duplicative of one another can also be employed. One is used to supply left ventricular action while the other is used to supply right ventricular action. The pumps can be operated independently since the computer can operate at sufficient speed to alternately control both of them through a round-robin distributor within the computer.

Having described the invention various modifications and improvements to the preferred embodiments can be made.

We claim:

1. In an extracorporeal ventricular support system for a patient having,
    a first chamber having an external wall with an opening to admit ambient air therethrough and including a first flexible bladder element and;
    an input port for fluidic coupling between said patient and said first bladder to allow free flow of blood from said patient through said port to said first bladder;
    a second chamber having a nonelastic outer wall and a second flexible bladder element contained within the volume enclosed by said non-elastic wall, the volume of said chamber external to said bladder being pneumatically sealed with respect to the interior of said bladder;
    first valve means coupled between said first and second bladders constructed to allow fluid flow between said first and second bladders only in the direction from said first toward said second bladder;
    an output port for conveying fluid from said second bladder to the arterial system of said patient;
    a second valve means coupled between said second bladder and said output port and constructed to pass fluid from said second bladder to said output port only in the direction from said second bladder toward said output port;
    said first and second chambers being positioned with respect to one another and to said patient so as to permit gravity flow from said input port through said first bladder into said second bladder;
    a pressurized gas source at substantially constant pressure;
    a controllable valve,
    a pneumatic line coupling the volume of said second chamber external to said bladder to said controllable valve,
    said controllable valve being operative in a first position to couple said gas source to the interior of said second chamber external to said bladder, and in a second position to vent the interior of said second chamber external to said bladder;
    means for sensing volumetric gas flow passing in a direction away from said second chamber toward said controllable valve and providing an output signal indicative of said gas flow, the improvement comprising;
    programmable means responsive to said signal indicative of the sensed gas flow to control said controllable valve to provide for a predetermined target output volume per beat from said pump by controlling the period said controllable valve is in said second position, so that it ends when said sensed gas flow decreases below a value indicating that blood inflow into said second chamber has substantially terminated.

2. A system in accordance with claim 1 wherein the period said valve is in said second position is terminated when said signal indicative of gas flow decreases below a predetermined value, and wherein the period when said valve is in said first position is determined by first establishing a predetermined period greater than required for a full stroke volume, and thereafter adjusting said period in decrements over several beats until said target volume is achieved.

3. A system in accordance with claim 2, wherein said period when said valve is in said first position is adjusted on the basis of measuring the integrated value of said flow signal during at least one previous diastolic period to serve as a measured volume per beat.

4. A system in accordance with claim 3 wherein, when said measured volume exceeds the target volume said predetermined period is decremented by a fixed amount of time for each beat until the target volume is achieved and wherein, when said measured volume is less than said target volume said period is incremented only at intervals which are the equivalent of several beat periods, until said target volume is reached.

5. A system in accordance with claim 1 including means for selecting a volumetric rate of flow output and adjusting the number of beats per unit time at said target output volume per beat to produce said selected volumetric flow.

6. A system in accordance with claim 5 wherein said number of beats is adjusted by increasing the period when said controllable valve is in said second position until said number of beats produces said selected volumetric rate of flow.

7. A system in accordance with claim 5 wherein said system reverts to a beat rate determined by said target volume per beat whenever said volumetric flow rate cannot be achieved.

8. A system in accordance with claim 6 wherein said volumetric rate of flow is measured by determining the average time said valve is in said first position and said second position, per stroke, and determining from this over a preset measuring period the beat rate of said pump, and multiplying by the stroke volume.

* * * * *